(12) United States Patent
Son

(10) Patent No.: US 10,655,131 B2
(45) Date of Patent: May 19, 2020

(54) APTAMER SPECIFICALLY BINDING TO L-ASCORBIC ACID AND USE OF THE SAME

(71) Applicant: NEXMOS Co., Ltd., Yongin-si (KR)

(72) Inventor: In-sik Son, Seongnam-si (KR)

(73) Assignee: NEXMOX Co., Ltd., Yongin-si (KR)

( * ) Notice: Subject to any disclaimer, the term of this patent is extended or adjusted under 35 U.S.C. 154(b) by 0 days.

(21) Appl. No.: 16/148,236

(22) Filed: Oct. 1, 2018

(65) Prior Publication Data

US 2019/0078094 A1 Mar. 14, 2019

Related U.S. Application Data

(63) Continuation-in-part of application No. 15/654,470, filed on Jul. 19, 2017, now Pat. No. 10,201,489, which is a continuation-in-part of application No. PCT/KR2017/002207, filed on Feb. 28, 2017.

(30) Foreign Application Priority Data

Mar. 4, 2016 (KR) .................. 10-2016-0026437
Aug. 30, 2018 (KR) .................. 10-2018-0102964

(51) Int. Cl.
C12N 15/115 (2010.01)

(52) U.S. Cl.
CPC ........ *C12N 15/115* (2013.01); *C12N 2310/16* (2013.01); *C12N 2310/334* (2013.01); *C12N 2310/336* (2013.01); *C12N 2310/531* (2013.01)

(58) Field of Classification Search
CPC .......................... C12N 15/115; C12N 2310/16
See application file for complete search history.

(56) References Cited

FOREIGN PATENT DOCUMENTS

| KR | 1013697160000 | | 3/2014 | |
|---|---|---|---|---|
| KR | 2016007931 | * | 1/2016 | |
| KR | 2018063935 | * | 6/2018 | |
| KR | 2019031705 | * | 3/2019 | |
| WO | WO-2018237074 A1 | * | 12/2018 | ........... C12N 15/115 |

OTHER PUBLICATIONS

English machine translation of KR 2016007931, pp. 1-17, retrieved on Oct. 18, 2019 (Year: 2016).*
English machine translation of KR2018063935, pp. 1-18, retrieved on Oct. 18, 2019 (Year: 2018).*
English machine translation of KR2019031705, pp. 1-16, retrieved on Oct. 18, 2019 (Year: 2019).*
Foreign Office Action issued from Korean Intellectual Property Office, dated Oct. 23, 2018, in response to Korean Patent application No. 10-2017-7027837.

* cited by examiner

*Primary Examiner* — Brian Whiteman

(57) ABSTRACT

The present invention relates to a single-stranded DNA aptamer which inhibits oxidation by binding to L-ascorbic acid, characterized in that the single stranded DNA aptamer has at least one of stem-loop structure, has CG bond at the end of the stem-loop structure, and both of the beginning parts of the stem-loop structure are G or C, in which the same bases are faced to each other. The aptamer of the present invention has an anti-oxidative effect of vitamin C, it can be used for functional cosmetics of various formulations, oral nutritional supplements, foods, etc. by maintaining the reduced state of vitamin C using the aptamer which selectively binds to vitamin C to maintain the anti-oxidative function of vitamin C for a long time. In addition, it can be anticipated that the anti-oxidative effect is continued and maximized even with a small amount of vitamin C by using the aptamer selectively binding to vitamin C.

4 Claims, 7 Drawing Sheets

Specification includes a Sequence Listing.

[Fig. 1]

Fig.4
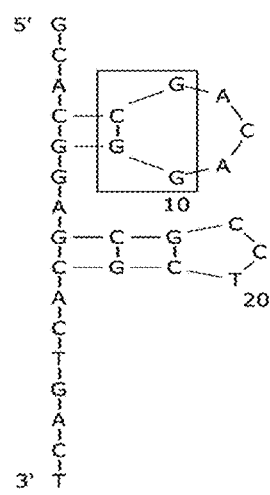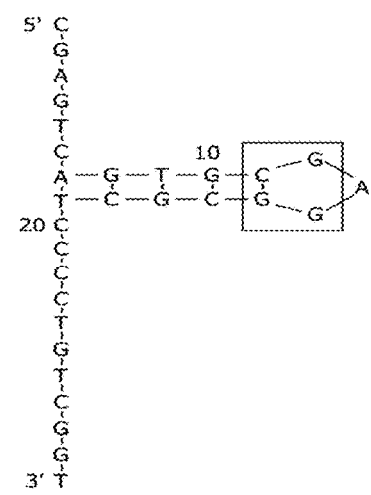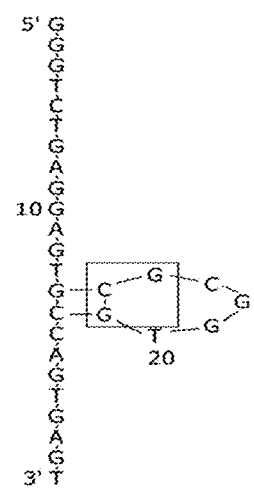

[Fig. 6]

SEQUENCE LISTING

<160> NUMBER OF SEQ ID NOS: 32

<210> SEQ ID NO 1
<211> LENGTH: 30
<212> TYPE: DNA
<213> ORGANISM: Artificial Sequence
<220> FEATURE:
<223> OTHER INFORMATION: aptamer

<400> SEQUENCE: 1
gcaccgacag gggagcgcct cgcactgact                30

```
<210> SEQ ID NO 2
<211> LENGTH: 30
<212> TYPE: DNA
<213> ORGANISM: Artificial Sequence
<220> FEATURE:
<223> OTHER INFORMATION: aptamer

<400> SEQUENCE: 2
ggtgcaaacc agcgcgcctc tctgacgtcg                                          30

<210> SEQ ID NO 3
<211> LENGTH: 30
<212> TYPE: DNA
<213> ORGANISM: Artificial Sequence
<220> FEATURE:
<223> OTHER INFORMATION: aptamer

<400> SEQUENCE: 3
acgcatgccg ggcgcgctcc ctgtcgtccg                                          30

<210> SEQ ID NO 4
<211> LENGTH: 30
<212> TYPE: DNA
<213> ORGANISM: Artificial Sequence
<220> FEATURE:
<223> OTHER INFORMATION: aptamer

<400> SEQUENCE: 4
cgagtcagtg cgaggcgctc ccctgtcggt                                          30

<210> SEQ ID NO 5
<211> LENGTH: 30
<212> TYPE: DNA
<213> ORGANISM: Artificial Sequence
<220> FEATURE:
<223> OTHER INFORMATION: aptamer

<400> SEQUENCE: 5
gggtctgagg agtgcgcggt gccagtgagt                                          30

<210> SEQ ID NO 6
<211> LENGTH: 30
<212> TYPE: DNA
<213> ORGANISM: Artificial Sequence
<220> FEATURE:
<223> OTHER INFORMATION: aptamer

<400> SEQUENCE: 6
gaaccaacgg aagcgcggca ccacaacggt                                          30

<210> SEQ ID NO 7
<211> LENGTH: 30
<212> TYPE: DNA
<213> ORGANISM: Artificial Sequence
<220> FEATURE:
<223> OTHER INFORMATION: aptamer

<400> SEQUENCE: 7
cgcaacctgt tcggcagtgg gcctccgggt                                          30

<210> SEQ ID NO 8
<211> LENGTH: 30
<212> TYPE: DNA
<213> ORGANISM: Artificial Sequence
<220> FEATURE:
<223> OTHER INFORMATION: aptamer
```

```
<400> SEQUENCE: 8
gaacttgcgc actaggtgat gcggatcccg                                            30

<210> SEQ ID NO 9
<211> LENGTH: 30
<212> TYPE: DNA
<213> ORGANISM: Artificial Sequence
<220> FEATURE:
<223> OTHER INFORMATION: aptamer

<400> SEQUENCE: 9
gaagcttgcg cactaggtgg tgcggatccc                                            30

<210> SEQ ID NO 10
<211> LENGTH: 30
<212> TYPE: DNA
<213> ORGANISM: Artificial Sequence
<220> FEATURE:
<223> OTHER INFORMATION: aptamer

<400> SEQUENCE: 10
gatcaacgga agcgcggcac cacaacggta                                            30

<210> SEQ ID NO 11
<211> LENGTH: 30
<212> TYPE: DNA
<213> ORGANISM: Artificial Sequence
<220> FEATURE:
<223> OTHER INFORMATION: aptamer

<400> SEQUENCE: 11
cgagtcaggt gggatgatgt tcggggaagg                                            30

<210> SEQ ID NO 12
<211> LENGTH: 30
<212> TYPE: DNA
<213> ORGANISM: Artificial Sequence
<220> FEATURE:
<223> OTHER INFORMATION: aptamer

<400> SEQUENCE: 12
ggcacaacgg gcgcgcctcc atgctgttcg                                            30

<210> SEQ ID NO 13
<211> LENGTH: 30
<212> TYPE: DNA
<213> ORGANISM: Artificial Sequence
<220> FEATURE:
<223> OTHER INFORMATION: aptamer

<400> SEQUENCE: 13
tgaacgacga ggcgcgtcac actgcgtgcc                                            30

<210> SEQ ID NO 14
<211> LENGTH: 30
<212> TYPE: DNA
<213> ORGANISM: Artificial Sequence
<220> FEATURE:
<223> OTHER INFORMATION: aptamer

<400> SEQUENCE: 14
cgcagtgtga cgcgcctcgt cgttcactcg                                            30

<210> SEQ ID NO 15
```

```
<211> LENGTH: 30
<212> TYPE: DNA
<213> ORGANISM: Artificial Sequence
<220> FEATURE:
<223> OTHER INFORMATION: aptamer

<400> SEQUENCE: 15
cacaatcggg gcgcgctcgt cctctggccg                                              30

<210> SEQ ID NO 16
<211> LENGTH: 30
<212> TYPE: DNA
<213> ORGANISM: Artificial Sequence
<220> FEATURE:
<223> OTHER INFORMATION: aptamer

<400> SEQUENCE: 16
ggaacaacgg gcgcgcctcc atgctgttcg                                              30

<210> SEQ ID NO 17
<211> LENGTH: 32
<212> TYPE: DNA
<213> ORGANISM: Artificial Sequence
<220> FEATURE:
<223> OTHER INFORMATION: aptamer

<400> SEQUENCE: 17
gtggaggcgg tggccagtct cgcggtggcg gc                                           32

<210> SEQ ID NO 18
<211> LENGTH: 32
<212> TYPE: DNA
<213> ORGANISM: Artificial Sequence
<220> FEATURE:
<223> OTHER INFORMATION: aptamer

<400> SEQUENCE: 18
gtggaggcgg tggccgtgga ggcggaggcc gc                                           32

<210> SEQ ID NO 19
<211> LENGTH: 32
<212> TYPE: DNA
<213> ORGANISM: Artificial Sequence
<220> FEATURE:
<223> OTHER INFORMATION: aptamer

<400> SEQUENCE: 19
gtggaggcgg tggccagtct gcggcgcggc ag                                           32

<210> SEQ ID NO 20
<211> LENGTH: 32
<212> TYPE: DNA
<213> ORGANISM: Artificial Sequence
<220> FEATURE:
<223> OTHER INFORMATION: aptamer

<400> SEQUENCE: 20
ggcggtggcc ctgcaagtct cgcggtggcg gc                                           32

<210> SEQ ID NO 21
<211> LENGTH: 32
<212> TYPE: DNA
<213> ORGANISM: Artificial Sequence
<220> FEATURE:
<223> OTHER INFORMATION: aptamer

<400> SEQUENCE: 21
```
ggcggtggcc ctggaagtct cgcggtggcg gc            32

<210> SEQ ID NO 22
<211> LENGTH: 32
<212> TYPE: DNA
<213> ORGANISM: Artificial Sequence
<220> FEATURE:
<223> OTHER INFORMATION: aptamer

<400> SEQUENCE: 22
gcggcggtgg ccagaagtct cgcggtggcg gc            32

<210> SEQ ID NO 23
<211> LENGTH: 32
<212> TYPE: DNA
<213> ORGANISM: Artificial Sequence
<220> FEATURE:
<223> OTHER INFORMATION: aptamer

<400> SEQUENCE: 23
cgggcggtgg ccagaagtct cgcggtggcg gc            32

<210> SEQ ID NO 24
<211> LENGTH: 32
<212> TYPE: DNA
<213> ORGANISM: Artificial Sequence
<220> FEATURE:
<223> OTHER INFORMATION: aptamer

<400> SEQUENCE: 24
gcggcggtgg cctgaagtct ggcggtggcc cg            32

<210> SEQ ID NO 25
<211> LENGTH: 32
<212> TYPE: DNA
<213> ORGANISM: Artificial Sequence
<220> FEATURE:
<223> OTHER INFORMATION: aptamer

<400> SEQUENCE: 25
gcggcggtgg cctgaagtct ggcggtggcc cc            32

<210> SEQ ID NO 26
<211> LENGTH: 32
<212> TYPE: DNA
<213> ORGANISM: Artificial Sequence
<220> FEATURE:
<223> OTHER INFORMATION: aptamer

<400> SEQUENCE: 26
gcggcggtgg cctgaagtct ggcggtggcc ca            32

<210> SEQ ID NO 27
<211> LENGTH: 32
<212> TYPE: DNA
<213> ORGANISM: Artificial Sequence
<220> FEATURE:
<223> OTHER INFORMATION: aptamer

<400> SEQUENCE: 27
ggcggtggcc tggaagtctc atggcggtgg cc            32

<210> SEQ ID NO 28
<211> LENGTH: 32
<212> TYPE: DNA

```
<213> ORGANISM: Artificial Sequence
<220> FEATURE:
<223> OTHER INFORMATION: aptamer

<400> SEQUENCE: 28
gtggcggtgg ccagcatacg ggcggtggcc ag                              32

<210> SEQ ID NO 29
<211> LENGTH: 32
<212> TYPE: DNA
<213> ORGANISM: Artificial Sequence
<220> FEATURE:
<223> OTHER INFORMATION: aptamer

<400> SEQUENCE: 29
gtggcggtgg ccagcatagt ggcggtggcc ag                              32

<210> SEQ ID NO 30
<211> LENGTH: 60
<212> TYPE: DNA
<213> ORGANISM: Artificial Sequence
<220> FEATURE:
<223> OTHER INFORMATION: SS DNA library
<220> FEATURE:
<221> NAME/KEY: misc_feature
<222> LOCATION: (16)..(45)
<223> OTHER INFORMATION: n is a, c, g, or t

<400> SEQUENCE: 30
atgcggatcc cgcgcnnnnn nnnnnnnnnn nnnnnnnnnn nnnnngcgcg aagcttgcgc    60

<210> SEQ ID NO 31
<211> LENGTH: 15
<212> TYPE: DNA
<213> ORGANISM: Artificial Sequence
<220> FEATURE:
<223> OTHER INFORMATION: primer

<400> SEQUENCE: 31
atgcggatcc cgcgc                                                 15

<210> SEQ ID NO 32
<211> LENGTH: 15
<212> TYPE: DNA
<213> ORGANISM: Artificial Sequence
<220> FEATURE:
<223> OTHER INFORMATION: primer

<400> SEQUENCE: 32
gcgcaagctt cgcgc                                                 15
```

APTAMER SPECIFICALLY BINDING TO L-ASCORBIC ACID AND USE OF THE SAME

TECHNICAL FIELD

The present invention relates to an aptamer specifically binding to L-Ascorbic acid and use of the same.

BACKGROUND ART

L-Ascorbic acid (Vitamin C, hereinafter, referred to as 'AA') which is one of representative components among antioxidants is widely used in medicine, cosmetics, food and beverage industries due to its antioxidant activity through neutralization of its free radicals. It was reported that the advantage of AA when AA is used as a food aid and/or medical active ingredient is to inhibit ZnONPs inhalation which may be generated in the industrial disaster (tire and rubber plants and plant for manufacturing cosmetics) by feeding drinking water adding AA during oxidation procedure of acute lung cells. Vitamin C is commonly used as a major solution in these industries, which cost tens of trillion wons.

AA can be easily degraded essentially by oxidation because of its antioxidant ability. The main factors affecting the oxidation of AA are temperature, pH, oxygen, metal ions, light, enzyme, and the like. In the industries using AA as a main ingredient, the oxidative-degradation property has been recognized as the present question for a long time because said property affects both the storage period and effect of the product due to said property. Therefore, many researches and costs are being invested in developing and discovering new and better methods as well as the understanding of the oxidative-degradation of AA in these industries.

Meanwhile, there are many reasons for promoting aging, but Reactive Oxygen [0004] species (ROS) is accepted as being one of significantly important causes. This active oxygen is indispensably produced in the energy metabolism process, immune response, etc., and it is an unavoidable stimulus which is also caused by the external harmful environment. The active oxygen has very high reactivity and leads to DNA deterioration, excessive signaling causing, protein deterioration, etc., and thus, leads to a series of reactions accumulating harmful effect on health. However, these harmful reactions are made to elaborately maintain their homeostasis by the antioxidant material (uric acid, vit. C, vit B, etc.) or antioxidant enzyme (Glutathione peroxidase, superoxide dismutase, catalase, etc.) present in vivo. However, an ageing of the antioxidant system according to endogenous aging and an accumulation of active oxygen by continuous harmful stimulus break such the balance, harm health, promote aging and cause various diseases such as skin diseases, skin cancer, arteriosclerosis and thrombosis (Laure Rittie et al., Ageing Research Reviews, 1, 705-720, 2002; Cutler R G, Annals of the New York Academy of Sciences, 1055, 93-135, 2005).

Accordingly, there are increasing interests in antioxidants that inhibit the formation of active oxygen systems or eliminate the formed active oxygen system. Antioxidants can be divided into two groups: a naturally occurring group in the body and an externally administered group. The naturally occurring group in the body includes enzymes such as superoxide dismutase (SOD), glutathione, peroxidase, catalase, etc., and the externally administered group includes phytochemicals such as kaempferol, catechin, genistein, etc.; vitamin E, vitamin C and beta-carotene; and minerals such as selenium, etc.

Cells are attacked by free radicals and oxygen free-radicals caused by ultraviolet A (UVA), and ultraviolet B (UVB) irradiated from sunlight, pollutants, stress, smoking, drinking, fatty foods, etc., and if the cells are not properly protected from such substances, they will be aged or dead. In the case of skin, the production of materials such as collagen or elastin, etc. is reduced or denatured by such substances, causing the skin to lose elasticity and to have wrinkles. In order to prevent this, it is known that it is important to prevent the aging of the skin by applying a preparation containing antioxidants such as vitamin A, C, E, etc., to the skin and absorbing it into the skin to prevent oxidation by the harmful active substances. However, synthetic vitamin C has a problem in manufacturing various formulations having a long storage period, due to the problem that it is easily oxidized in the air and its antioxidant effect disappears.

Vitamin C, which has a very high reducing power, reacts very sensitively to substances with high oxidation potential and thus, vitamin C is rapidly oxidized. It is well-known that vitamin C is oxidized and its effect is impaired. Water has a high oxidation potential, so vitamin C is very sensitively reacted with it and is rapidly oxidized.

Therefore, needs for new methods or materials for inhibiting the oxidation of antioxidants, including vitamin C, have existed for a long time.

In addition, the prevention of oxidation of antioxidants using an aptamer is an approach of safe and innovative new concept compared to the conventional methods, and it can be manufactured to maximize the effect by applying it to various industries. In particular, it will be a catalyst for transforming the existing chemical-based cosmetics, nutritional supplements, and food markets into DNA (BIO)-based markets. In the future, it is expected to provide explosive growths and innovative solutions in the DNA markets.

PRIOR PATENT REFERENCE

Korean Laid-open Patent Application No. 10-2018-0054508

DISCLOSURE

Technical Problem

The present invention is made by the above mentioned needs, and the object of the present invention is to provide new aptamer preventing oxidation by specifically binding to vitamin C.

The other object of the present invention is to provide a use of the new aptamer mentioned above.

Technical Solution

In order to achieve the above objects, the present invention provides a single-stranded DNA aptamer binding to L-ascorbic acid to inhibit oxidation, which is characterized in that the single stranded DNA aptamer has at least one stem-loop structure, the end of the stem structure of the stem-loop structure has CG bond and both beginning parts of the loop structure are G or C, in which the same bases are faced to each other.

The aptamer of the present invention is provided as a single-stranded DNA aptamer having a CG bond at the end of the stem structure of the stem loop structure and having a secondary structure in which G or C base in one direction at the beginning part of the loop structure is substituted with T.

In one embodiment of the present invention, the aptamer is preferably consisted of one of the base sequences shown in SEQ ID NOS: 1 to 29, and more preferably the above-mentioned aptamer is consisted of one of the base sequences shown in SEQ ID NO: 1, SEQ ID NO: 4, SEQ ID NO: 5, and SEQ ID NOS.: 17-29, but is not limited thereto.

The present invention also provides a composition for antioxidation, comprising the aptamer of the present invention as an effective ingredient.

In addition, the present invention provides a method for inhibiting the oxidation of vitamin C by treating the vitamin C with the aptamer of the present invention.

Advantageous Effects

As can be seen from the present invention, the aptamer of the present invention has an antioxidant effect of vitamin C and keeps the antioxidant function for a long time by maintaining the reduced state of vitamin C using an aptamer that selectively binds to vitamin C (ascorbic acid) and thus can be used for functional cosmetics of various formulations, dietary supplements, etc., and it can be anticipated to have continuous and maximized antioxidant effects even with a small amount of vitamin C by using the aptamer selectively binding to vitamin C. In addition, it can be used for various health beverages, antioxidant drinks, antioxidant foods, etc. by maintaining the reduced state of the physiologically active ingredients such as vitamin C, etc. with the aptamer which selectively binds to vitamin C (ascorbic acid) to keep the antioxidant function for a long time.

In addition, the prevention of oxidation of antioxidants by using an aptamer is an approach of safe and innovative new concept compared to the conventional methods, and it can be manufactured so as to be applied to various industries and to be effective. In particular, it will be a catalyst for transforming the existing chemical-based cosmetics, nutritional supplements, and food markets into a DNA (BIO)-based markets. In the future, it is expected to provide the explosive growths and innovative solutions in the DNA markets.

DESCRIPTION OF DRAWINGS

FIG. 4 is a secondary folding structure of an aptamer using an M-fold program. The stem-loop structure of SEQ ID NO: 1, SEQ ID NO: 4 and SEQ ID NO: 5 has common characteristics that it has a CG bond at the end of the stem structure and has G or C in both of the beginning parts of the loop structure, in which the same bases are faced to each other (Red square).

MODE FOR INVENTION

Hereinafter, the present invention will be described in detail with reference to Examples. However, the following examples are described for illustrative purposes only and the scope of the present invention is not construed as being limited by the following Examples.

Example 1: Preparation of a Single Stranded DNA Library

A single-stranded DNA library was constructed to screen single-stranded DNA aptamers specifically binding to L-Ascorbic acid using the SELEX method. Single-stranded DNA library sequences were consisted of a total of 60 bases, each containing 15 specific primer sequences at 5' and 3' and having 30 random sequences.

The single stranded DNA library as designed above is as follows.

```
5'-ATGCGGATCCCGCGC-N30-GCGCGAAGCTTGCGC-3'
(single stranded DNA library sequence;
SEQ ID NO: 30)
```

A single stranded DNA library was amplified by an asymmetric PCR procedure using a single oligonucleotide fragment of the synthesized base sequence of SEQ ID NO: 30 as a template. Primers 1 and 2 were constructed to perform the asymmetric PCR.

The base sequences of primers 1 and 2 above are as follows:

```
                             (Primer 1; SEQ ID. NO: 31)
5'-ATGCGGATCCCGCGC-3'

(Primer 2; SEQ ID. NO: 32)
5'-GCGCAAGCTTCGCGC-3'
```

Figure 1:
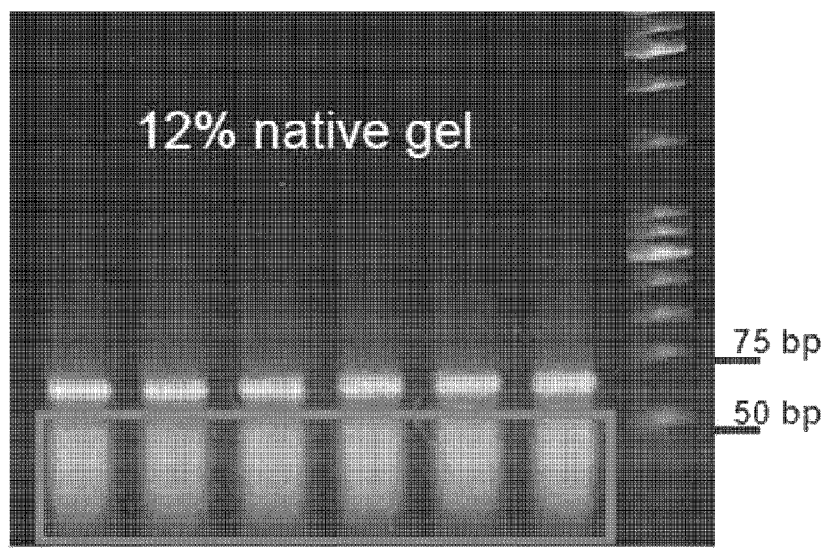
FIG. 1 is a photograph of 12% native gel electrophoresis used for isolating a single stranded DNA library. The band indicated by blue squares was cut and purified by the Crush and Soak method.

The asymmetric PCR was performed by mixing Primer 1 and Primer 2 in a ratio of 10:1 in order to amplify a large amount of single stranded DNA. The asymmetric PCR reaction was amplified by reacting it at 94° C. for 5 minutes, followed by repeatedly carrying out 45 cycles under the condition of 94° C. for 40 seconds, 55° C. for 40 seconds, 72° C. for 30 seconds, followed by reacting it at 72° C. for 10 minutes. The amplified PCR product was elctrophoresed on a 2.5% agarose gel, and the band was visually confirmed at first and then separated by the Crush and Soak method. The PCR product was electrophoresed on 12% native gel, the single-stranded DNA bands were cut, and then dissolved in Crush and Soak buffer (500 mM NH$_4$OAc, 0.1% SDS, 0.1 mM EDTA) and DNA was purified with Ethanol precipitation method (FIG. 1). The purified single-stranded DNA library was heated at 95° C. for 5 minutes, and then formed the folded structure at room temperature for 10 minutes and then used in SELEX.

Example 2: Selex for Selection of Aptamers Specifically Binding to L-Ascorbic Acid In order to select the single stranded DNA aptamers that specifically bind to L-ascorbic acid to inhibit oxidation, SELEX (rGO-SELEX) technology using graphene was utilized (Lee, A. Y., Ha, N. R., Jung, I. P., Kim, S. H., Kim, A. R., & Yoon, M. Y. (2017). Development of a ssDNA aptamer for detection of residual benzylpenicillin. Analytical biochemistry, 531, 1-7.).

Hereinafter, the SELEX method using graphene is as follows.

At first, in order to remove the single-stranded DNA non-specifically binding to graphene and 1.5-ml tube, 200 pmol of single-stranded DNA library and 4 mg/mL of graphene were mixed in a binding buffer (20 mM Tris, pH 8.0), reacted for 30 minutes, and then the supernatant was removed by two centrifugations. The remaining single-stranded DNA and graphene mixtures was treated with ascorbic acid for 30 min to react them, and the single-stranded DNA bound to ascorbic acid was amplified by the asymmetric PCR procedure. The amplified single-stranded DNA was isolated by the Crush and Soak method at 12% native gel and was obtained as the first SELEX product. The above procedure was repeated 5 times and the symmetric PCR was performed by using the $5^{th}$ repeated SELEX product as a template. The amplified double-stranded DNA fragments were sequenced by Next Generation Sequencing (NGS) technology to identify 16 sequences of SEQ ID NOS: 1 to 16, which are analyzed at a high frequency.

Example 3: Assay for the Antioxidant Effect of Ascorbic Acid phenylenediamine (OPDA) assay was performed to analyze the antioxidant effect of L-ascorbic acid by an aptamer. The antioxidant effect of ascorbic acid by the aptamer was analyzed by using the principle that DHA, which is an oxidized structure of L-ascorbic acid, binds to OPDA to develop fluorescence (Vislisel, J. M., Schafer, F. Q., & Buettner, G. R. (2007). A simple and sensitive assay for ascorbate using a plate reader. Analytical biochemistry, 365(1), 31-39.).

The OPDA analysis procedure is as follows.

Figure 2:
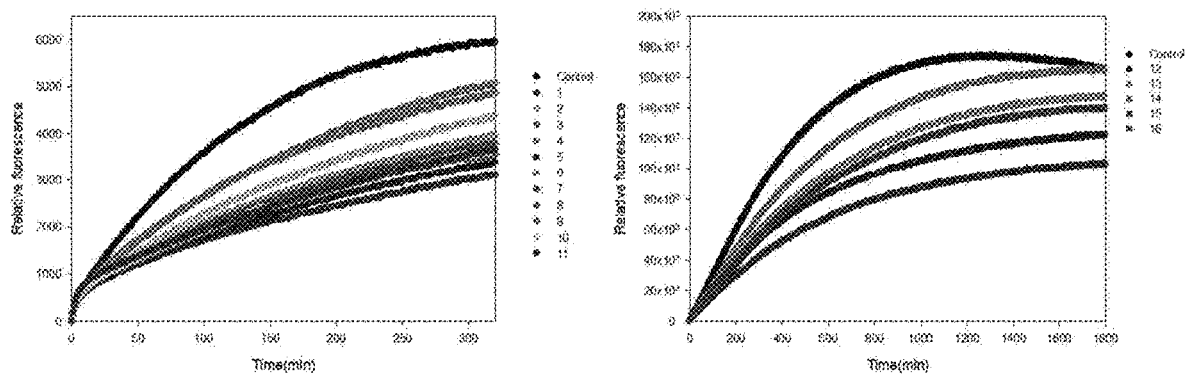
FIG. 2 is an OPDA measurement graph for identifying ascorbic acid-antioxidant effect of single stranded DNA. The antioxidant effect was observed in the single stranded DNA of SEQ ID NO: 1, SEQ ID NO: 4 and SEQ ID NO: 5.

Sixteen sequences were synthesized according to the frequency and folding structure of the sequence analyzed by NGS technology in SELEX products. The synthesized single-stranded DNA was heated at 95° C. for 5 minutes and reacted at room temperature for 10 minutes to form a folded structure. Then, 1 µM of single stranded DNA and 5 mM ascorbic acid were mixed and reacted for 30 minutes. Then, hydrogen peroxide ($H_2O_2$) was added to accelerate the oxidation and then the fluorescence intensity was measured by adding OPDA fluorescent dye (Non-Patent Document 3). A control was a sample adding only vitamin C without adding the synthesized single stranded DNA and was oxidized more rapidly than the samples treated with the single stranded DNA of 16 sequences (SEQ ID NOS: 1 to 16). It was observed that oxidation of L-ascorbic acid was prevented in three single stranded DNAs of SEQ ID NO: 1, SEQ ID NO: 4 and SEQ ID NO: 5 among the 16 sequences (FIG. 2).

Example 4: Measurement of the Binding Force Between L-Ascorbic Acid and Aptamer Sequence The binding dissociation constant (Kd) was measured using a Microscale Thermophoresis (MST) method to confirm the binding force of the aptamer binding to L-ascorbic acid. Fluorescence of Cy5 was attached to 5' of the single-stranded DNA and the intensity of binding was measured by analyzing the signal difference depending on the binding force under thermal gradient conditions (Entzian, C., & Schubert, T. (2016). Studying small molecule-aptamer interactions using MicroScale Thermophoresis (MST). Methods, 97, 27-34.).

Figure 3:
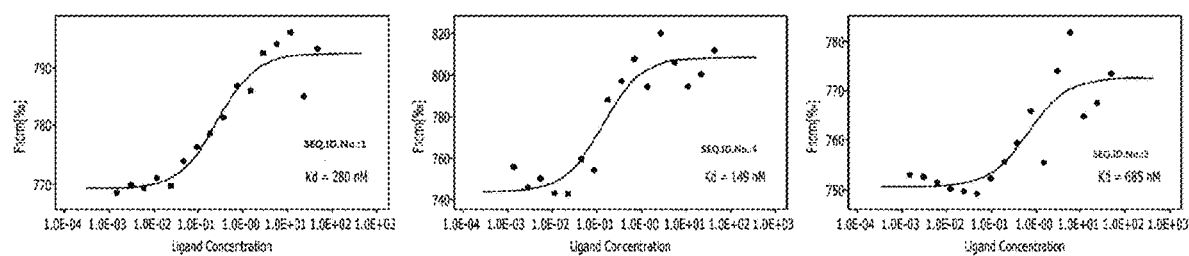
FIG. 3 is a graph of Microscale Thermophoresis (MST) measurement results of selected single stranded DNA. As a result of the binding dissociation constant (Kd) measurement, the binding force was confirmed at the level of nano molarity (nM) in the single stranded DNA of SEQ ID NO: 1, SEQ ID NO: 4 and SEQ ID NO: 5.

The concentration of single stranded DNA aptamer was fixed at 5 nM and ascorbic acid was added to 16 tubes in a concentration gradient ranging from 50 uM to 1.53 nM and then reacted for 15 minutes. The reacted single-stranded DNA and L-ascorbic acid were inhaled into a scanning capillary tube (4 ul/tube) and then measured using a Monolith NT.11 instrument. The aptamers of SEQ ID NO: 1, SEQ ID NO: 4 and SEQ ID NO: 5 confirmed by the above OPDA method were measured to have Kd values of 280 nM, 149 nM and 685 nM, respectively, and thus identified as being a binding force of the level of nano molarity (nM) (FIG. 3).

Example 5: Analysis for the Structural Similarity of Single Stranded DNA Aptamer Specifically Binding to Vitamin C M-fold program was used to identify the secondary structure of the single-stranded DNA aptamers of SEQ ID NO: 1. SEQ ID NO: 4 and SEQ ID NO: 5 the binding power of which was identified. In the case of SEQ ID NO: 1, it is possible to form a secondary structure in two forms, and it was identified that SEQ ID NO: 4 and SEQ ID NO: 5 could form a stem-loop structures in three or two forms, respectively.

These three single-stranded DNA aptamers (SEQ ID NO: 1, SEQ ID NO: 4 and SEQ ID NO: 5) are characterized in that they have a CG bond at the end of stem structure of the stem-loop structure and have G or C which is faced to each other at both of the beginning parts of the loop structure (FIG. 4, red squares). The structures of the three identified aptamers have stable structures with a Gibbs free energy values of −3.65 and −1.64, −0.86 (kcal/mol), respectively.

Example 6: Measurement of Antioxidant Effect of 13 Variant Sequences

Figure 5:
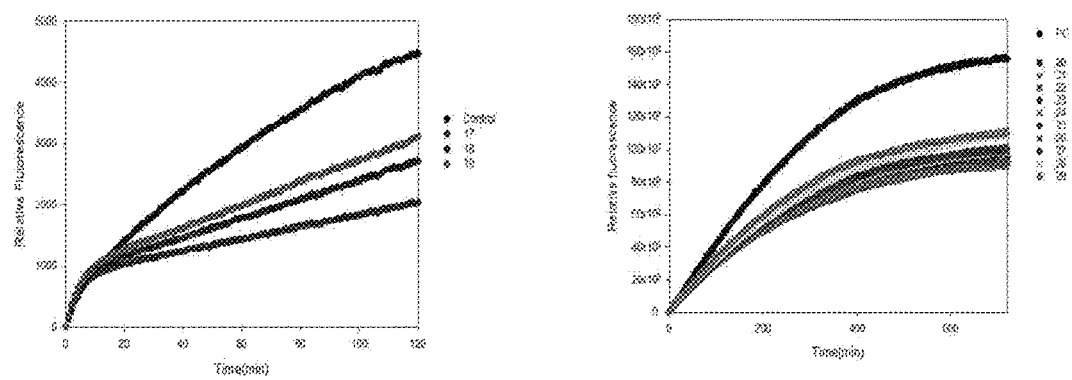
FIG. 5 is a graph of OPDA measurements for 13 optional sequences including a stem-loop structure. The antioxidant effect of ascorbic acid was observed in 13 sequences including a specific stem-loop structure.

Single stranded DNA was synthesized by designing arbitrary sequences of 32 base sequences based on the specific structural sequences identified through analysis of folding structure of aptamer. An arbitrary single-stranded DNA was prepared so that 10 base sequences were constituted as a unit in a stem-loop structure to be comprised 1-2 of them at both 5' and 3' ends. The antioxidant effects of the single stranded DNAs of SEQ ID NOS: 17 to 29, which were prepared in 13 kinds, were confirmed through the OPDA assay (FIG. 5).

Figure 6:
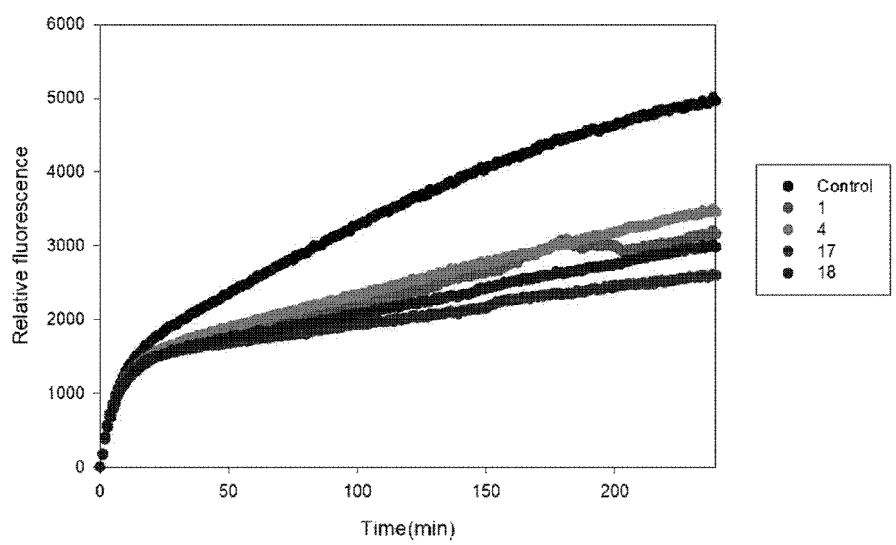
FIG. 6 is a comparative graph of OPDA measurement for SEQ ID NOS: 1, 4, 17, and 18 for which the antioxidant effect was confirmed. It was observed that the aptamer sequence of SEQ ID NO: 17 has the greatest antioxidant effect.

All of the 13 random sequences had antioxidant effects against L-ascorbic acid, and the single-stranded DNA aptamer of SEQ ID NO: 17 with a stem-loop structure at both ends of 5' and 3' was identified as having the greatest anti-oxidative effect among the total of 29 sequences (13 sequences which were arbitrarily synthesized and identified, and 16 sequences which were selected by the SELEX process) (FIG. 6).

Example 7: Kd Measurement and Comparison of Two Modified Sequences

Figure 7:
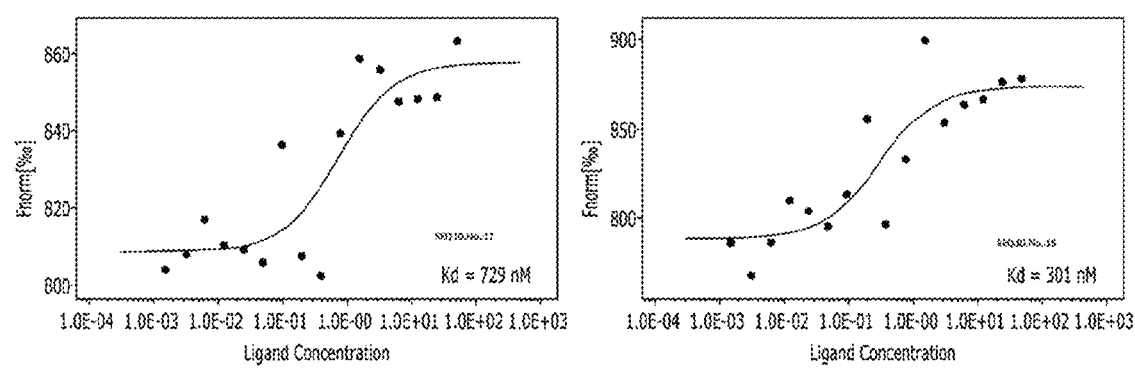
FIG. 7 is a graph showing MST measurement results of SEQ ID NOs: 17 and 18 for which the antioxidant effect is confirmed.

The binding force of the aptamer was confirmed by MST (Microscale Thermophoresis) analysis for two sequences in which the anti-oxidative effect was confirmed as being high among arbitrary sequences (SEQ ID NOS: 17 to 29). Sequences of SEQ ID NOS: 17 and 18 identified by the OPDA method obtained the measurement values as Kd values of 729 nM and 289 nM, respectively (FIG. 7). Unlike the result identified by the OPDA measurement method, the Kd value of SEQ ID NO: 17 was determined as being high, seemingly indicating that the aptamer of SEQ ID NO: 17 had a low binding force but more specifically bound to the —OH functional group.

TABLE 1

| SEQ. ID. NOS. | 5' to 3' | Number of base (mer) | Note |
|---|---|---|---|
| SEQ. ID. No: 1 | GCACCGACAGGGGAGCGCCTCGCACTGACT | 30 | ABA1 |
| SEQ. ID. No: 2 | GGTGCAAACCAGCGCGCCTCTCTGACGTCG | 30 | ABA2 |
| SEQ. ID. No: 3 | ACGCATGCCGGGCGCGCTCCCTGTCGTCCG | 30 | ABA3 |
| SEQ. ID. No: 4 | CGAGTCAGTGCGAGGCGCTCCCCTGTCGGT | 30 | ABA4 |
| SEQ. ID. No: 5 | GGGTCTGAGGAGTGCGCGGTGCCAGTGAGT | 30 | AA-001 |
| SEQ. ID. No: 6 | GAACCAACGGAAGCGCGGCACCACAACGGT | 30 | AA-002 |
| SEQ. ID. No: 7 | CGCAACCTGTTCGGCAGTGGGCCTCCGGGT | 30 | AA-003 |
| SEQ. ID. No: 8 | GAACTTGCGCACTAGGTGATGCGGATCCCG | 30 | AA-005 |
| SEQ. ID. No: 9 | GAAGCTTGCGCACTAGGTGGTGCGGATCCC | 30 | AA-006 |
| SEQ. ID. No: 10 | GATCAACGGAAGCGCGGCACCACAACGGTA | 30 | AA-014 |
| SEQ. ID. No: 11 | CGAGTCAGGTGGGATGATGTTCGGGGAAGG | 30 | AA-035 |

TABLE 1 -continued

| SEQ. ID. NOS. | 5' to 3' | Number of base (mer) | Note |
|---|---|---|---|
| SEQ. ID. No: 12 | GGCACAACGGGCGCGCCTCCATGCTGTTCG | 30 | AAL-1 |
| SEQ. ID. No: 13 | TGAACGACGAGGCGCGTCACACTGCGTGCC | 30 | AAL-2 |
| SEQ. ID. No: 14 | CGCAGTGTGACGCGCCTCGTCGTTCACTCG | 30 | AAL-3 |
| SEQ. ID. No: 15 | CACAATCGGGGCGCGCTCGTCCTCTGGCCG | 30 | AAL-4 |
| SEQ. ID. No: 16 | GGAACAACGGGCGCGCCTCCATGCTGTTCG | 30 | AAL-5 |
| SEQ. ID. No: 17 | GTGGAGGCGGTGGCCAGTCTCGCGGTGGCGGC | 32 | 332-2 |
| SEQ. ID. No: 18 | GTGGAGGCGGTGGCCGTGGAGGCGGAGGCCGC | 32 | 332-4 |
| SEQ. ID. No: 19 | GTGGAGGCGGTGGCCAGTCTGCGGCGCGGCAG | 32 | 332-8 |
| SEQ. ID. No: 20 | GGCGGTGGCCCTGCAAGTCTCGCGGTGGCGGC | 32 | 332-11 |
| SEQ. ID. No: 21 | GGCGGTGGCCCTGGAAGTCTCGCGGTGGCGGC | 32 | 332-12 |
| SEQ. ID. No: 22 | GCGGCGGTGGCCAGAAGTCTCGCGGTGGCGGC | 32 | 332-13 |
| SEQ. ID. No: 23 | CGGGCGGTGGCCAGAAGTCTCGCGGTGGCGGC | 32 | 332-14 |
| SEQ. ID. No: 24 | GCGGCGGTGGCCTGAAGTCTGGCGGTGGCCCG | 32 | 332-15 |
| SEQ. ID. No: 25 | GCGGCGGTGGCCTGAAGTCTGGCGGTGGCCCC | 32 | 332-16 |
| SEQ. ID. No: 26 | GCGGCGGTGGCCTGAAGTCTGGCGGTGGCCCA | 32 | 332-17 |
| SEQ. ID. No: 27 | GGCGGTGGCCTGGAAGTCTCATGGCGGTGGCC | 32 | 332-18 |
| SEQ. ID. No: 28 | GTGGCGGTGGCCAGCATACGGGCGGTGGCCAG | 32 | 332-19 |
| SEQ. ID. No: 29 | GTGGCGGTGGCCAGCATAGTGGCGGTGGCCAG | 32 | 332-20 |

Table 1 shows the aptamer sequences of the present invention.

What is claimed is:

1. A single-stranded DNA aptamer which inhibits oxidation by binding to L-ascorbic acid,
the single stranded DNA aptamer having at least one from 5' to 3' end direction CG-N1-XG step-loop structure, wherein C is prior to an unpaired loop sequence G-N1-X in which N1 is any of 1 to 3 nucleotides and X is G or T, and G is subsequent to the unpaired loop sequence and forms a C-G bond with the C.

2. The single-stranded DNA aptamer of claim 1, the DNA aptamer comprises a nucleotide sequence selected from the group consisting of SEQ ID NOS: 1, 4, 5, 17, 22, 23 and 26.

3. An anti-oxidative composition comprising the aptamer of claim 1 as an active ingredient.

4. A method for inhibiting oxidation of vitamin C by treating the vitamin C with the aptamer of claim 1.

* * * * *